(12) United States Patent
Priore et al.

(10) Patent No.: US 8,862,445 B2
(45) Date of Patent: Oct. 14, 2014

(54) SELECTING SPECTRAL ELEMENTS AND COMPONENTS FOR OPTICAL ANALYSIS SYSTEMS

(75) Inventors: Ryan J. Priore, Columbia, SC (US); Robert P. Freese, Pittsboro, NC (US); Michael L. Myrick, Irmo, SC (US); John C. Blackburn, Charleston, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 1728 days.

(21) Appl. No.: 12/094,466

(22) PCT Filed: Nov. 27, 2006

(86) PCT No.: PCT/US2006/045436
§ 371 (c)(1), (2), (4) Date: Oct. 6, 2008

(87) PCT Pub. No.: WO2007/062224
PCT Pub. Date: May 31, 2007

(65) Prior Publication Data
US 2009/0216504 A1 Aug. 27, 2009

Related U.S. Application Data

(60) Provisional application No. 60/740,044, filed on Nov. 28, 2005.

(51) Int. Cl.
| | |
|---|---|
| G06F 7/60 | (2006.01) |
| G06F 17/10 | (2006.01) |
| G06G 7/48 | (2006.01) |
| G06F 17/50 | (2006.01) |
| G01N 21/27 | (2006.01) |
| G01J 3/08 | (2006.01) |
| G01J 3/02 | (2006.01) |
| G01N 21/31 | (2006.01) |
| G01J 3/28 | (2006.01) |
| G06F 17/18 | (2006.01) |

(52) U.S. Cl.
CPC ............... *G01J 3/28* (2013.01); *G06F 17/5009* (2013.01); *G01N 21/274* (2013.01); *G06F 17/5086* (2013.01); *G01J 3/08* (2013.01); *G01J 3/02* (2013.01); *G01N 21/31* (2013.01); *G01J 3/0232* (2013.01); *G01J 3/0291* (2013.01); *G01J 3/0286* (2013.01); *G01J 3/021* (2013.01); *G06F 17/50* (2013.01); *G06F 17/18* (2013.01); *G01J 3/0208* (2013.01)
USPC .................................................. 703/6; 703/2

(58) Field of Classification Search
CPC . G06F 17/50; G06F 17/5009; G06F 17/5086; G06F 17/18
USPC ........................................................ 703/2, 6
See application file for complete search history.

(56) References Cited

U.S. PATENT DOCUMENTS

| | | | | |
|---|---|---|---|---|
| 6,950,492 | B2 * | 9/2005 | Besson | 378/5 |
| 7,652,765 | B1 * | 1/2010 | Geshwind et al. | 356/330 |

(Continued)

OTHER PUBLICATIONS

H. Swierenga, "Strategy for constructing robust multivariate calibration models", Elsevier, 1999.*

*Primary Examiner* — Thai Phan
*Assistant Examiner* — Angel Calle
(74) *Attorney, Agent, or Firm* — Haynes and Boone, LLP (57) ABSTRACT

Methods of selecting spectral elements and system components for a multivariate optical analysis system include providing spectral calibration data for a sample of interest; identifying a plurality of combinations of system components; modeling performance of a pilot system with one of the combinations of system components; determining optimal characteristics of the pilot system; and selecting optimal system components from among the combinations of system components.

19 Claims, 8 Drawing Sheets

(56) References Cited

U.S. PATENT DOCUMENTS 7,671,973 B2 * 3/2010 Van Beek et al. ............... 356/39
2005/0024640 A1 * 2/2005 Fateley et al. ................. 356/330
2005/0222833 A1 * 10/2005 Kropaczek et al. ............. 703/18
2006/0181700 A1 * 8/2006 Andrews et al. ........... 356/237.2

* cited by examiner

| detector | wave range ($\lambda \mu$m) |
|---|---|
| Pt-S | 0.35 - 0.6 |
| Si p-n PD | 0.4 - 1.0 |
| Si p-i-n PD | 0.4 - 1.1 |
| Si APD | 0.4 - 0.8 |
| Ge p-n PD | 0.6 - 1.8 |
| InSb p-n PD | 3.0 - 6.2 |
| PbSnTe p-n PD | 5.0 - 11.4 |
| PbS | 0.5 - 3.8 |
| PbSe | 0.8 - 4.6 |
| PbTe | 0.8 - 5.5 |
| p - InSb | 2.0 - 6.7 |
| n - InSb | 1.0 - 3.6 |
| PbSnTe | 5.0 - 11.0 |
| CdHgTe | 5.0 - 16.0 |
| Ge:Au | 2.0 - 9.5 |
| Ge:Zn,Au | 5.0 - 40.0 |
| Ge:Cu | 5.0 - 30.0 |
| Si:Al | 2.0 - 16.0 |
| Si:Sb | 2.0 - 31.5 |
| ATGS | 1 - 1000 |
| (Ba,Sr)TiO$_3$ | 1 - 1000 |
| Si | 0.2 - 1.1 |
| Ge | 0.4 - 1.8 |
| InAs | 1.0 - 3.8 |
| InSb | 1.0 - 7.0 |
| InSb (77K) | 1.0 - 5.6 |
| HgCdTe (77K) | 1.0 - 25.0 |
| PbS | 1.0 - 3.0 |
| InGaAs | 1.0 - 1.9 |
| PbSe | 1.0 - 4.0 |

FIG. 7

| Properties of Select Infrared Transmitting Materials for Transmission Spectroscopy ||||||||||
|---|---|---|---|---|---|---|---|---|
| Material | Comments | SWL cm-1 | LWL cm-1 | RI | Solubility g/100g | Hardness Kg/mm2 | MP °C | pH Range |
| AMTIR | SeAsGe glass, brittle | 11000 | 593 | 2.5 | 0 | 170 | 370 | 1-9 |
| BaF2 | Barium Flouride | 66600 | 691 | 1.45 | 0.17 | 82 | 1280 | 5-8 |
| CaF2 | Calcium Flouride | 79500 | 896 | 1.4 | 0.0017 | 158 | 1360 | 5-8 |
| CsI | Cesium Iodide, very hygroscopic, Somewhat Toxic | 42000 | 172 | 1.73 | 44 | 20 | 621 | NA |
| Diamond | Type IIa, strong IR absorbance between 2700-1800 cm-1, costly | 30000 | <2 | 2.4 | 0 | 5700 | 550 fp | 1-14 |
| Ge | Germanium, brittle, becomes opaque at elevated temperatures | 5500 | 432 | 4 | 0 | 780 | 936 | 1-14 |
| KBr | Potassium Bromide, most widely used for mid-IR applications | 48800 | 345 | 1.52 | 53 | 6 | 730 | NA |
| KCl | Potassium Chloride | 55600 | 385 | 1.45 | 35 | 7 | 776 | NA |
| KRS-5 | Thallium Bromide / Thallium Iodide, Extremely Toxic | 17900 | 204 | 2.37 | 0.05 | 40 | 414 | 5-8 |
| NaCl | Sodium Chloride | 52600 | 457 | 1.49 | 36 | 18 | 801 | NA |
| Polyethylene | For Far-IR, swells with some organic solvents | 625 | <4 | 1.52 | 0 |  | 110 | 1.5-14 |
| Sio 2 | Silicon Dioxide | 50000 | 2315 | 1.53 | 0 | 460 | 1713 | 1-14 |
| SI | Silicon, strong IR absorbance between 624-590 cm-1 | 8900 | 624,30 | 3.41 | 0 | 1150 | 1420 | 1-12 |
| ZoS | Zinc Sulfide | 17000 | 690 | 2.2 | 0 | 240 | 1830 | 5-9 |
| ZnSe | Zinc Selinide | 15000 | 461 | 2.4 | 0 | 120 | 1526 | 5-9 |
| H2O | Water | — | — | — | — | — | — | — |
| D2O | Deuterium Oxide | — | — | — | — | — | — | — |
| SWL- Shortest wavelength for transmission, 1mm 50% transmission ||||||||||
| LWL- Longest wavelength for transmission, 1mm 50% transmission ||||||||||
| RI- Refractive Index, at relevant wavelength ||||||||||
| MP- Melting point ||||||||||
| pH- negative log of hydrogen ion concentration ||||||||||

FIG. 8

SELECTING SPECTRAL ELEMENTS AND COMPONENTS FOR OPTICAL ANALYSIS SYSTEMS

CROSS-REFERENCE TO RELATED APPLICATIONS

This application claims benefit of and priority to U.S. Provisional Patent Application, Ser. No. 60/740,044, filed Nov. 28, 2005; incorporated herein by reference in its entirety.

BACKGROUND OF THE DISCLOSURE

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{("Equation 1")}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n, z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{(``Equation 2'')}$$

where y is octane rating, $a_n$ are constants determined by the regression analysis, and $x_1$, $x_2$, $X_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \quad \text{(``Equation 3'')}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOE(s)). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters, digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most Important wavelengths. While the detector Integrates or coadds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

BRIEF SUMMARY OF THE DISCLOSURE

The present disclosure is directed generally to an optical system for multivariate optical computing (MOC), which is generally described in U.S. Pat. No. 6,198,531 B1 to Myrick et al. and in U.S. Pat. No. 6,529,276 B1 to Myrick as a predictive spectroscopy technique that incorporates a multi-wavelength spectral weighting directly into analytical instrumentation. Both of these patents are incorporated herein for all purposes by reference thereto.

The present disclosure more particularly provides systems and methods for deriving information from light. For example, processes for selecting particular spectral elements and components for the optical analysis system are described herein.

According to one aspect of the disclosure, a method of selecting spectral elements and system components for a multivariate optical analysis may include providing spectral calibration data for a sample of interest; identifying a plurality of combinations of system components; modeling performance of a pilot system with one of the combinations of system components; determining a prediction accuracy of the pilot system; determining an optimal signal-to-noise ratio of the pilot system; and selecting optimal system components from among the combinations of system components. The sample of interest may be a chemical mixture, a chemical compound or a chemical liquid solution. The mixture may be a powder, particulates or the like, and may be mixed in a liquid.

Also in this aspect, the system components may include detectors, light sources, spectral elements including multivariate spectral elements, other optical components and combinations of these and other components, devices and elements useful in an optical analysis system.

Further in this aspect of the disclosure, the performance may be modeled using multivariate optical analysis, and/or modeled by designing a multivariate optical element for the sample of interest.

Also in this aspect of the disclosure, the spectral calibration data and design data related to the multivariate optical element may be combined. A standard error of calibration may be provided, and the exemplary method may include optimizing within a limitation of the multivariate optical element to determine optimal spectral elements for the sample of interest. The method may further include producing a standard error of prediction and optimizing within a limitation of the multivariate optical element to determine optimal spectral elements for the sample of interest. In this aspect, the performance may be an overall system performance or a multivariate optical element performance.

The system components in this aspect may include a plurality of detectors, and the optimal signal-to-noise ratio may be determined by evaluating expected signal levels and using a noise equivalent power of the detectors as a noise level.

The system components in this aspect may include a plurality of detectors and the optimal signal-to-noise ratio may be determined by evaluating an expected signal level and using photon-limited noise where photon noise associated with the signal level is sufficiently high to overwhelm detector noise.

Further in this aspect of the disclosure, the method may include ranking the system components relative to each other to select an optimal system. The method may also include manufacturing the optimal system.

According to another aspect of the disclosure, a method of selecting spectral elements and system components for a multivariate optical analysis system may include providing spectral calibration data for a sample of interest; identifying a plurality of combinations of system components; modeling performance of a pilot system with one of the combinations of system components; determining optimal characteristics of the pilot system; and selecting optimal system components from among the combinations of system components. In this aspect, determining optimal characteristics may include determining a prediction accuracy of the pilot system and/or determining an optimal signal-to-noise ratio of the pilot system.

According to yet another aspect of the disclosure, a method of selecting spectral elements and system components for a multivariate optical analysis system may include providing spectral calibration data for a sample of interest; identifying a plurality of combinations of system components; modeling performance of a pilot system with one of the combinations of system components using a multivariate optical analysis; determining optimal characteristics of the pilot system; selecting optimal system components from among the combinations of system components; and manufacturing an optimal system. In this aspect, determining optimal characteristics may include determining a prediction accuracy of the pilot system and/or determining optimal characteristics includes determining an optimal signal-to-noise ratio of the pilot system.

Also in this aspect of the disclosure, the system components may include detectors, light sources, spectral elements including multivariate spectral elements, other optical components and combinations of these and other components, devices and elements useful in an optical analysis system.

Additional objects and advantages of the present subject matter are set forth in, or will be apparent to those of ordinary skill in the art, from the detailed description herein. Also, it should be further appreciated that modifications and variations to the specifically illustrated, referred and discussed features and elements hereof may be practiced in various embodiments and uses thereof without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present subject matter, including the best mode thereof to one skilled in the art, is set forth more particularly in the remainder of the specification, including reference to the accompanying figures, in which:

FIG. 8 is a table of exemplary spectral elements that may be used according to various aspects of the present disclosure.

DETAILED DESCRIPTION OF THE DISCLOSURE

Detailed reference will now be made to the drawings in which examples embodying the present subject matter are shown. The detailed description uses numerical and letter designations to refer to features of the drawings. Like or similar designations of the drawings and description have been used to refer to like or similar parts of the disclosure.

The drawings and detailed description provide a full and written description of the examples in the disclosure, and of the manner and process of making and using those examples, so as to enable one skilled in the pertinent art to make and use them, as well as the best mode of carrying out the examples. However, the examples set forth in the drawings and detailed description are provided by way of explanation only and are not meant as limitations of the disclosure. The present disclosure thus includes any modifications and variations of the following examples as come within the scope of the appended claims and their equivalents.

Figure 1:
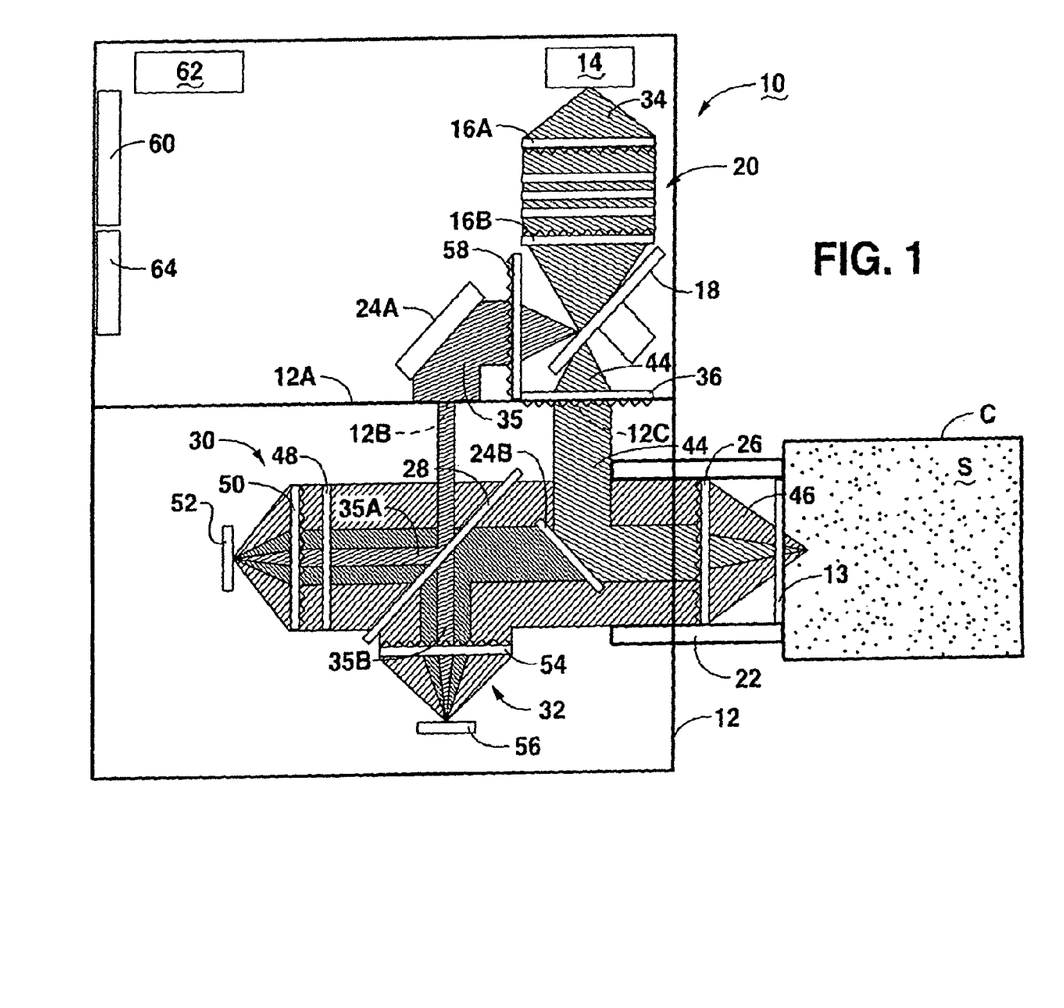
FIG. 1 is a schematic plan view of an optical analysis system according to an aspect of the disclosure.

With reference now to FIG. 1, an exemplary embodiment of the present subject matter is designated generally by reference number 10. As shown, the optical analysis system 10 broadly includes a housing 12, an illumination or light source 14, a chopper wheel 18, one or more spectral elements 20, a focusing lens 26, a beam splitter 28, a first detector assembly 30 including a multivariate optical element 48, and a second detector assembly 32 including a detector 56. The optical analysis system 10 further includes an electrical connection 60, a pressurization sensor 62 and a purge gas assembly 64, which those skilled in the art will readily understand; therefore, further description is not necessary to understand and practice these aspects of the disclosure.

Also shown in FIG. 1, the illumination source 14 provides a light 34, which passes through a collecting Fresnel lens 16A and into and through the spectral element(s) 20. In this example, the illumination source 14 is rated for at least about 10,000 hours of operation, which alleviates a need for redundant illumination sources though they may be provided if desired. Also in this example, the collecting Fresnel lens 16A is sized to be about 1.5 square inches and is spaced about 0.6 inches from the illumination source 14. The skilled artisan will instantly recognize that these dimensions can be adjusted according to particular system requirements and are not meant as limitations of the disclosure.

As further shown in FIG. 1, the light 34 passes through the spectral elements 20, which filter out undesired wavelengths to define a desired spectral region, e.g., 1500-2000 nm, in order to target a particular chemical material of interest. The light 34 is focused by another focusing Fresnel lens 16B, which is also sized to be about 1.5 square inches and spaced about 1 inch from the chopper wheel 18. As shown, the chopper wheel 18 reflects a portion of the light 34 as a calibration or reference light 35 and a transmitted light 44. The calibration light 35 is collimated by a lens 58 before reflecting from a first mirror 24A through an adjustable aperture 12B in a bulkhead 12A of the housing 12. The aperture 12B is adjustable to dictate a desired amount of the calibration light 35. Finally, the calibration light 35 impinges on the beam splitter 28 thereby sending a portion 35A of the calibration light 35 to the first MOE detector 30 and a portion 35B of the calibration light 35 to the second or baseline detector 32.

FIG. 1 further illustrates that the transmitted light 44 passes from the chopper wheel 18 into a collimating Fresnel lens 36, which in this example is sized to be about 1.5 square inches and is spaced about 0.6 inches from the chopper wheel 18. The transmitted light 44 passes through another adjustable aperture 12C in the bulkhead 12A and impinges upon a second mirror 24B, which directs the transmitted light 44 toward a sample S in a container C, such as mixing vat or blender. The skilled artisan will recognize that the container C could be a conveyor belt or other device for holding or transporting the sample S and is not limited to an enclosed container. Likewise, the sample S can be a moving mixture such as aspirin and an excipient being blended in real time, a plurality of tablets passing by on a conveyor belt at high speed, a solution and the like.

As further shown in FIG. 1, the chopper wheel 18 modulates the light signal 44 (between about 50 to about 5000 Hz) to enable the photodetectors 52, 56 to perform properly. For example, the system 10 may be operated with a 10-window chopper wheel 18 rotating at 40 Hz and providing a chopped signal of 400 Hz. The chopper frequency is chosen based on several variables, including the rate of motion of the sample material S past the sampling window 13, the performance characteristic of the photodetectors 52, 56 and an amplification system, the sampling rate of the data collection and analysis system and the physical properties of the chopper motor, control system, and the chopper wheel 18 (including window materials).

The number of windows in the chopper wheel 18 can be adjusted to provide a desired degree of signal modulation. For example, the chopper 18 may include open windows and black spokes, the latter blocking the light 44. By way of further example, different materials can be placed in the windows to provide different spectral characteristics for the various windows. These window materials may be partially or completely transmissive to the light signal 44. The transmission characteristics of these windows may permit the windows to be used as spectral elements. These windows can also contain MOEs.

With continued reference to FIG. 1, the transmitted light 44 is focused by the focusing Fresnel lens 26, which in this example may be round and about $15/16$ inches in diameter. The lens 26 may also be adjustable within an inner tube 22. Also in this example, the lens 26 may be positioned about 0.6 inches from an outer surface of the container-C.

As further shown in FIG. 1, the transmitted light 44—now focused—passes through the transmissive window 13, which in this example is approximately 1 inch in diameter. Also, an anti-reflective (AR) coating may be applied on one or both sides of the lens 26 to ensure that a chemical process in the container C does not interfere with the measuring process of the optical analysis system 10. Thus, the transmitted light 44 enters the container C and reflects from the sample S as a carrier light 46.

FIG. 1 further illustrates that the carrier light 46 is directed by the tube 22 in a direction of the first detector assembly 30. Eventually, the carrier light 46 impinges on the beam splitter 28 and a portion passes in a direction of the detector assembly 32 and the detector 56 for baselining with the portion 35B of the calibration light 35. Another portion of the carrier light 46 passes through MOE 48, which as noted above, has been selected for the sample S (chemical of interest) based on the various components of the system 10. Finally, that portion of the carrier light 46, having passed through the MOE 48, is focused by the lens 50 and received by the detector 52.

As introduced above, the two signals collected by the detectors 52 and 56 can be manipulated, e.g., mathematically, to extract and ascertain information about the sample S carried by the carrier light 46. More specifically, as the light reaches the beam splitter 18, the light beam 34 is divided into a neutral or gray spectrum and a portion of the light ("signal A") is sent through the lens 54 onto the one detector 56 and a portion of the light ("signal B") is sent through the MOE 48, through the other lens 50 and onto the detector 52. The system 10 measures signal A and signal B, and a ratio of the two signals can be used to measure a concentration of the chemical of interest S. Additionally, monitoring of signal A and/or signal B independently, or in some combination, can provide other information, such as powder segregation, packing of materials, effect of particle size, etc. Any algebraic combination of signals A and B can be used; e.g., A and/or B independently; A divided by B; A plus B; A minus B; B divided by A; B minus A, etcetera. For example, a ratio of signal A to signal B can provide a chemical measurement; individually, A signal and/or B signal can provide other homogeneity measures including physical make-up of the sample, packing, particle size, and/or separate physical and chemical properties.

An auto-calibration process in accordance with the present subject matter may be implemented to confirm the signals A and B independently or the ratio of A and B. The auto-calibration process according to the present technology may be performed according to several different methodologies. The following methods are exemplary of the possible methodologies and are not intended as limitations on the full range of methods that may be employed.

It will be recalled that a portion of the overall system includes a chopper wheel as shown in FIG. 1. Rotation of the chopper wheel modulates the light impinging on the sample and hence the photodetector. A first method of the auto-calibration process involves placing a single known material in one or more of the chopper windows. A second method of the auto-calibration process involves providing different known materials in several of the chopper windows. In accordance with the first and second methods, by having knowledge of the composition of the material(s) in the chopper windows, the signal coming from the detector can be determined. It should be appreciated that, in general, it is not a requirement of the present technology to provide a specific number of windows in the chopper wheel. By using multiple calibration materials in the chopper wheel, several calibration parameters in the control software can be set, confirmed, or verified, essentially one per calibration material.

A third calibration method of the auto-calibration process involves a movable mirror (see FIG. 1), positioned so that, either by turning or horizontal displacement, the light that is normally directed down a sampling tube would be directed toward the beam splitter and hence the detectors without encountering the sample. The mirror can be positioned so that the illumination light beam is directed down the sampling tube toward the sample focusing lens. During calibration, the mirror is turned toward a second position. In this second position, the light is directed from the illumination source and the chopper wheel to the beamsplitter and then to the detectors by way of the beam splitter.

In one embodiment of a movable mirror methodology, a mirror assembly is configured to move horizontally with a mirror angled to direct light down the sampling tube and a mirror angled to direct light toward the beamsplitter. During normal sampling, the mirror may be positioned in a first position and for calibration, the mirror would be moved.

It should be appreciated that it may be necessary to adjust the gain on the detectors to measure the light from this "bypass." Alternatively, calibration materials that transmit a lower amount of light can be chosen so that the detectors can be kept at the same gains used for measuring the sample. Detectors provide an increased output signal dependent upon the amount of light impinging on them. As such, there is a preferred operating region for the detectors and subsequent amplification of the signal such that the final output does vary with the amount of impinging light. For instance, there are levels of light that are too low to produce a reliable output signal. In addition, there are levels of light that are too great and overload the detection system. At these high light levels, changes in the amount of light do not change the output signal. The preferred mode of operation is where the amount of light is in the range where there is a good correlation between the amount of light and the output signal of the detector system.

In accordance with the present auto-calibration technology, light is directed from the illumination sources to the detectors without interacting with the sample. Depending upon the type of sample being analyzed and the transmission characteristic of the light path between the illumination source, the sample, and the detectors, there can be a range of signals returned to the detector. As an example, the light path could include a fiber optic probe or the sample could be a powder being measured in a reflectance mode. In both of these examples, the amount of light returning to the detectors during normal sampling could be significantly less than the amount of light following the by-pass or calibration route to the detectors. In an exemplary configuration, light transmission through a sample may be reduced from 50-99.9%. Thus, in order to enable the detector and amplification system to operate over a useful range, some attenuation of the signal in the calibration elements may be needed.

In accordance with the present auto-calibration technology, a fourth calibration methodology involves providing an element in a chopper wheel that turns the light path slightly in addition to having a known spectral characteristic. Light can be directed to a reflective surface that sends light to a beam splitter and then to detectors. A particular aspect to this embodiment is that it allows for a continuous or real time check of the instrument calibration with each rotation of chopper wheel. In accordance with this method, a stationary mirror assembly allows the un-deflected beam to pass to the sample for sample measurements and the deflected beam to be directed toward the detection system without passing through or encountering the sample.

Turning now to FIGS. 2, 3, 4 and 5, another embodiment of an optical analysis system, generally designated by the element number 110, is provided. Many aspects of the optical analysis system 110 and its related components are similar to the foregoing embodiment; thus, for the sake of brevity, only certain differences are described below. To provide a full and enabling disclosure of the optical analysis system 110, when like or similar elements and components are not specifically described below, implicit reference is made to the foregoing description.

Figure 2:
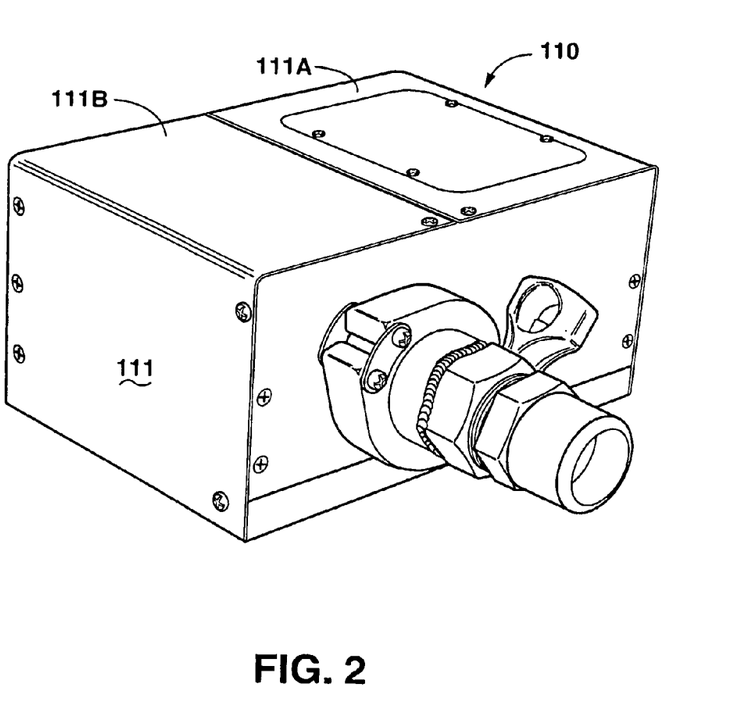
FIG. 2 is a perspective view of an optical analysis system according to another aspect of the disclosure.

As shown in FIG. 2, the system 110 is contained in a box or housing 111, which completely encloses the system 110. Thus, the system 110 can be used in a dangerous, explosive environment. In general, a hazard level of the environment in which the system 110 must operate will determine the level of containment needed; thus, the housing 111 can be made of stainless steel, plastic or other desired material as required by the operating environment. As shown, the housing 111 is divided into a lamp side 111A and a detector side 112A, which are described in detail below with respect to FIGS. 4 and 5 respectively. As noted with respect to system 10 above, the system 110 accomplishes sampling through a window similar to the window W above; i.e., transmissive in a spectral region of interest.

Figure 3:
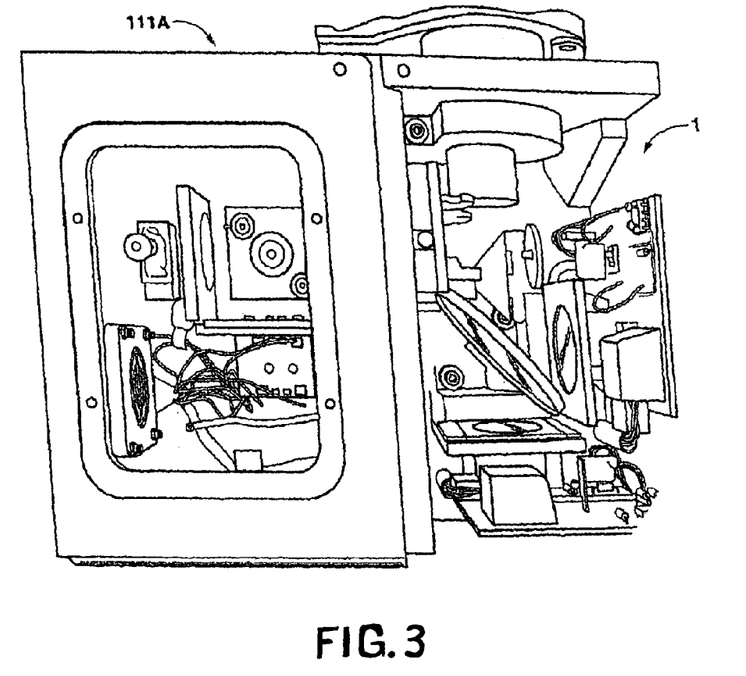
FIG. 3 is a partial cut-away plan view of the optical analysis system as in FIG. 2.
Figure 4:
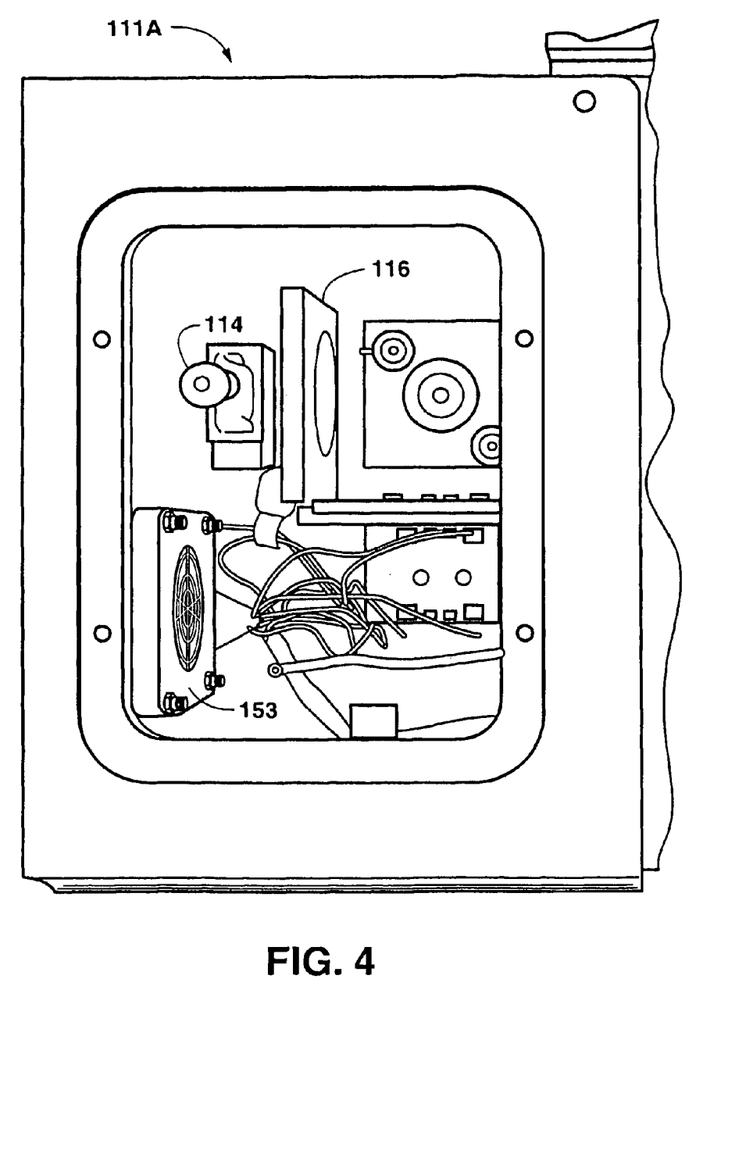
FIG. 4 is partial cut-away plan view of a lamp side of the optical analysis system as in FIG. 2.
Figure 5:
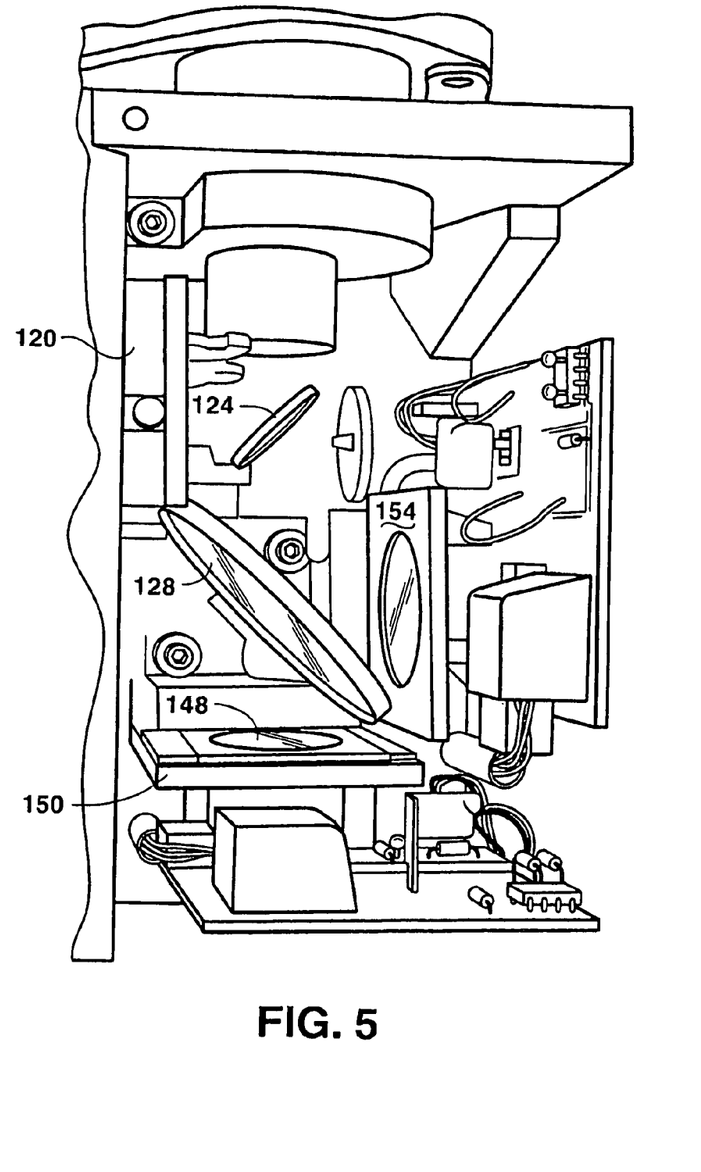
FIG. 5 is partial cut-away plan view of a detector side of the optical analysis system as in FIG. 2.

With reference to FIGS. 3, 4 and 5, detailed views of components of the system 110 are provided. FIG. 3 shows portions of the housing 11 removed to reveal the lamp side 111A and the detector side 111B in detail. FIG. 4 most clearly shows the lamp side 111A with an illumination source or lamp 114; a lens 116; and a cooling unit or fan 153. FIG. 5 most clearly shows a plurality of spectral elements 120; a mirror 124; a beam splitter 128; an MOE 148; and lenses 150, 154. These and other components are substantially as described above with respect to the foregoing embodiment.

Figure 6:
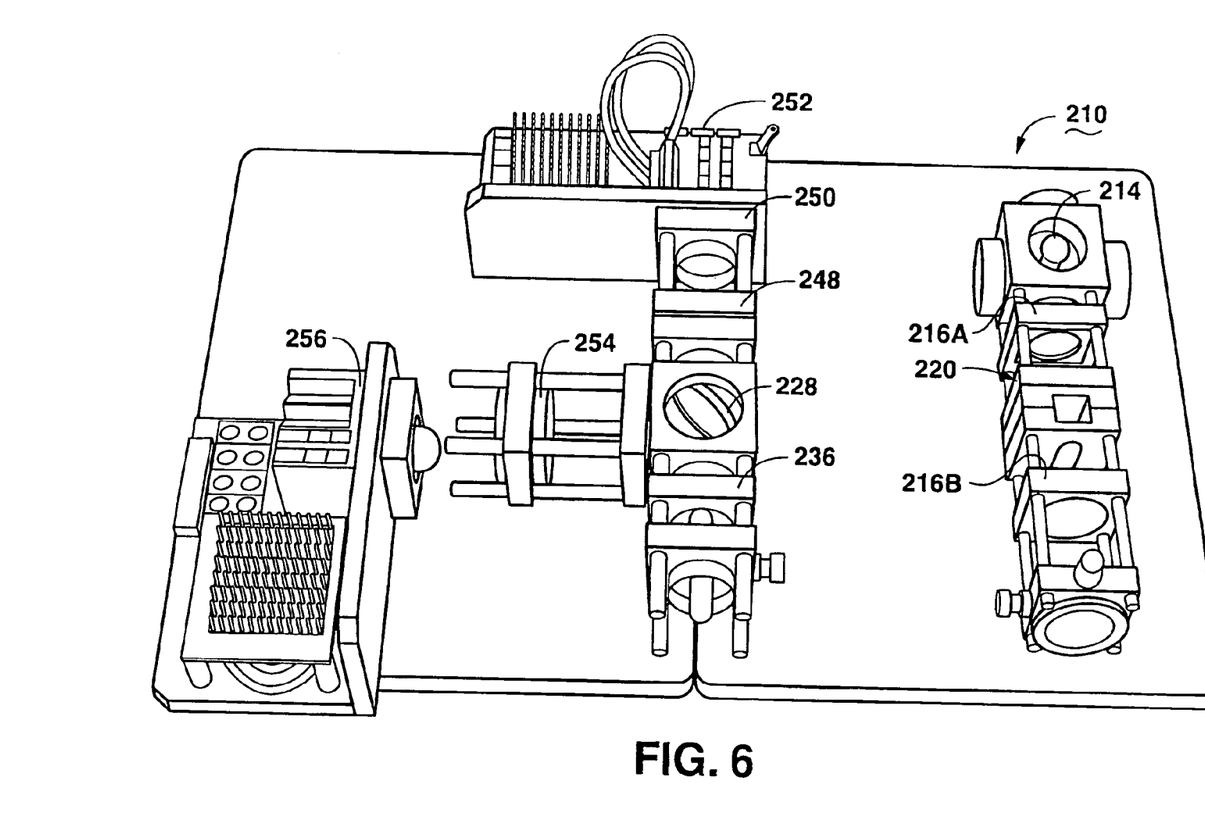
FIG. 6 is perspective view of an optical analysis system according to yet another aspect of the disclosure.

FIG. 6 shows a breadboard embodiment of an optical analysis system, generally designated by the element number 210, which is described by way of exemplary operation below. Many aspects of the optical analysis system 210 and its related components are similar to the foregoing embodiment; thus, for the sake of brevity, only certain differences are described below. However, to provide a full and enabling disclosure of the optical analysis system 210, when like or similar elements and components are not specifically described below, implicit reference is made to the foregoing description.

As shown in FIG. 6, an illumination source or lamp 214 is provided substantially as described above. Also shown are a lens 216A; a plurality of spectral elements 220; another lens 216B; a lens 236; a beamsplitter 228; an MOE 248; a lens 250 and a detector 252. A third lens 254 is also shown in communication with a detector 256. These and other components are substantially as described above with respect to the foregoing embodiment.

Figure 7:
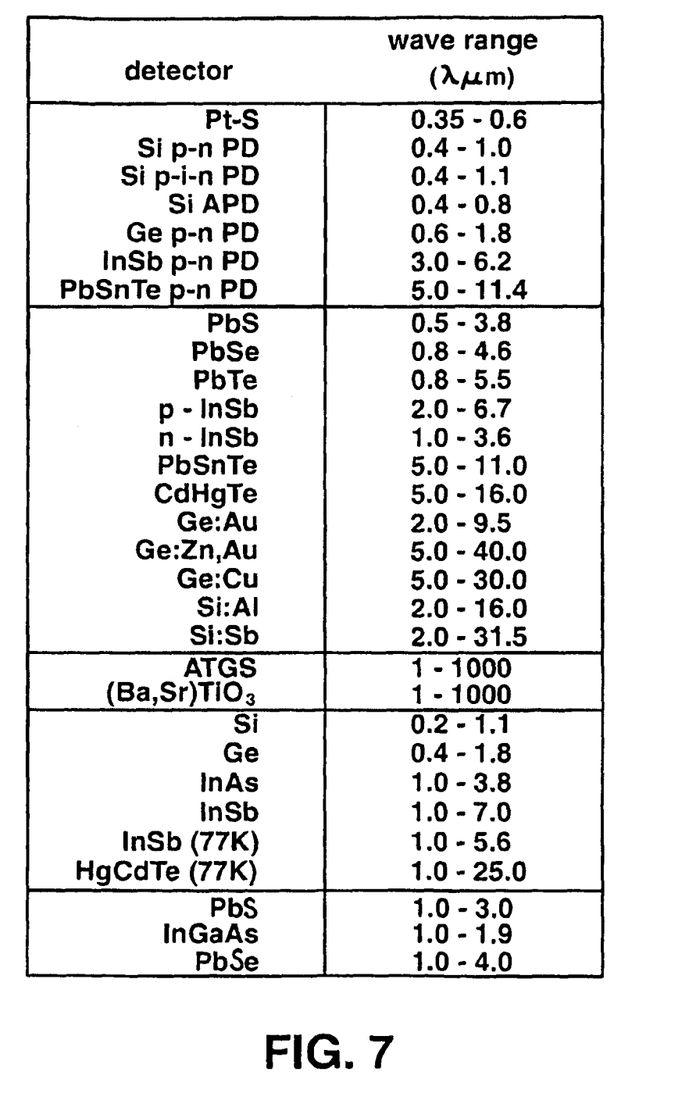
FIG. 7 is a table of exemplary detectors that may be used in the optical analysis system as in FIG. 1.

The tables shown in FIGS. 7 and 8 list various materials, which can be used in the spectral elements, detectors and windows described herein. For instance, when developing MOEs for a near infrared application of an optical analysis system, materials with some optically absorbing character may be used as one or more layers of the MOEs. Some examples of absorbing materials or films are shown in FIGS. 7 and 8, which include but are not limited to, silicon, germanium, sapphire, and doped versions thereof. Selection of these optical materials depends on the spectral region being measured.

More specifically, measurement precision can be shown to vary from an optimum value when transmittances are as low as practical to a poorer performance when overall transmittance is high. Absorbing films make it possible to engineer optical elements that meet the criteria of having strong variations in transmission at the most important wavelengths of a measurement (determined by a design algorithm) while maintaining low transmission at wavelengths that matter least in a measurement. The use of absorbing materials for optical elements thus provides an additional variable that can be controlled in the design and manufacture of the elements to reduce transmission in the desired spectral region. With a non-absorbing material, particular spectral regions can be transmissive or reflective. When an absorptive material is used, an element can be designed to be transmissive, reflective, or absorbing in a given spectral region, which provides expanded design parameters.

With further reference to FIG. 8, spectral ranges of various crystal materials are listed. As shown, the crystals have different spectral ranges for transmission sampling. In mid-IR, for example, the cutoff at low wavenumbers varies from approximately 896 cm-1 for CaF2 to 4 cm-1 for polyethylene. To some extent, the cutoff values may also be affected by the thickness of a particular crystal. The skilled artisan will understand that to convert from wavenumber (cm-1) to wavelength (μm) as shown In FIG. 8, 10,000 is divided by the wavenumber such that, e.g., 5500 cm-1 is equivalent to 1.8 μm or 1800 nm.

The embodiments of the disclosure may be better understood with reference to an exemplary process for selecting spectral elements and components for the systems and to operational examples.

As introduced above, a process for identifying the proper combination of system elements to make an optimally performing system must take into account multiple variables.

Specifically, the available types of detectors, light sources, optics and filtering elements make it possible to generate instruments with a wide range of combinations of components. A mathematical analysis can be used to analyze all possible combinations of these elements with the specific spectral calibration information available for a chemical measurement and render determinations of two important properties before a system is ever built. The results of these analyses are then used to determine the overall optical system configuration to use to provide the best performance.

The first of these properties of the complete system is the model performance. Model performance is the "best" possible performance for a system with the components selected in a particular combination. It can be arrived at by either a conventional multivariate analysis (manually or using an automated approach to modeling), or by designing multivariate optical elements for the specific chemical measurement. The model performance can be calculated using the spectroscopic calibration data for the system being measured. These calibration data are combined with the spectral elements under consideration. A multivariate analysis of the combined data can be used to produce a Standard Error of Calibration and Standard Error of Prediction. These results can be optimized within the limitations of the choice of spectral elements to determine the best combination of spectral elements for the particular measurement.

The second of the important properties that can be determined mathematically is the optimal signal to noise of the instrument. This can be estimated by evaluating the signal levels expected and using the noise equivalent power of the detectors as the noise level, or—if the signals are high enough to overwhelm the detector noise with photon noise—the photon-limited noise. The signal to noise for the expected system can be determined mathematically for the various system configurations under consideration. A system with a high signal to noise ratio will be predicted to have more useful and reliable measurement capability.

The measurement precision can be estimated by mathematical equation in either a detector-limited or photon-limited situation. Measurement precision is given by the standard deviation of the chemical measurement caused by detection noise, not by model error. The two things—model and measurement precision error—work together to define the best theoretical quality of measurement, and these factors can be estimated without actually making an instrument.

Given an estimate of these two important factors, the many possible combinations of detectors, light sources, spectral elements and optical components can be ranked against one another to select the optimal system before a system is manufactured. This selection process provides a method to identify the preferred system configuration for making the measurements of interest.

EXAMPLES

The following configurations are provided to illustrate various aspects of the disclosure and are not intended to limit the broader scope of the subject matter. These various optical configurations were used to make measurements on several different chemical mixtures.

Example 1

The breadboard system 210 introduced above with respect to FIG. 6 was used to measure concentrations of various sample mixture S. The system 210 was configured based on the mixture S being tested. An exemplary configuration of the system 210 included:
  Illumination: 20 w GILWAY lamp
  Spectral elements: 5 mm deuterium oxide ($D_2O$), 5 mm Germanium
  Optical window: fiber optic probe
  Detector: InAr detector from Judson
  MOE: specific to test Example 2

The system 110 introduced above with respect to FIG. 2 was used to make measurements on a mixture of aspirin and lactose as well as various other sample mixture S. The system 110 was configured based on the mixture being tested. The aspirin/lactose testing was performed using static testing in which the powdered sample with a known composition was placed in a dish and the system light beam was focused on the powdered sample. The output of the detectors was monitored and recorded. The aspirin/lactose samples covering the range of 100% aspirin to 100% lactose were tested. An exemplary configuration of the system 110 included:
  Illumination: 20 w GILWAY lamp
  Spectral elements: 5 mm D2O, 5 mm Germanium
  Optical window: none
  Detector: PbS detector from New England Photoconductor
  MOE: specific to test conditions Example 3

The system 110 was used again to make measurements on a mixture of aspirin and lactose. The system 110 was configured based on the mixture being tested. The aspirin/lactose testing was performed using dynamic conditions in which the lactose powder was placed in the bowl of a mixer and the measurement system was attached to the bowl using a Swagelok® brand connector/fitting. A sapphire window was used to contain the powder in the bowl and allow the system 110 to interrogate the powder. With the mixer turning, known amounts of aspirin were added and the system output signal was monitored and recorded. Aspirin was added in several allotments to about 37% final aspirin concentration. The configuration of the system 110 used in this example included:
  Illumination: 20 w Gilway lamp
  Spectral elements: 5 mm D2O, 5 mm Germanium
  Optical window: sapphire window
  Detector: PbS detector from New England Photoconductor
  MOE: specific to test conditions Example 4

A unit similar to the system 110 can be used to perform measurements of various sample mixtures in both static and dynamic modes. One configuration of this system included:
  Illumination: 5 w GILWAY lamp
  Spectral elements: 5 mm D2O, 5 mm Germanium
  Optical window: none
  Detector: PbS detector from New England Photoconductor
  MOE: specific to test conditions While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject That which is claimed is:

1. A method of selecting spectral elements and system components for a multivariate optical analysis system, the method comprising:
   (a) providing spectral calibration data for a sample of interest;
   (b) identifying a plurality of different combinations of system components selected from the group consisting of detectors, light sources, spectral elements, and optical components;
   (c) obtaining modeling performance of a pilot system with one of the combinations of system components;
   (d) determining a prediction accuracy of the pilot system utilized in step (c);
   (e) determining a signal-to-noise ratio of the pilot system utilized in step (c);
   (f) repeating steps (c), (d) and (e) for each of the plurality of combinations identified in step (b); and
   (g) selecting optimal system components from among the plurality of combinations of system components based on optimal signal-to-noise ratio.

2. The method as in claim 1, wherein the sample of interest is one of a chemical mixture, a chemical compound or a chemical liquid solution.

3. The method as in claim 1, wherein the performance is modeled using a multivariate optical analysis.

4. The method as in claim 1, wherein the performance is modeled by designing a multivariate optical element for the sample of interest and utilizing the multivariate optical element as a system component in step (b).

5. The method as in claim 4, further comprising generating design data related to the multivariate optical element and combining the spectral calibration data and multivariate optical element design data.

6. The method as in claim 5, further comprising calculating a standard error of calibration and optimizing within a limitation of the multivariate optical element to determine optimal spectral elements for the sample of interest.

7. The method as in claim 5, further comprising calculating a standard error of prediction and optimizing within a limitation of the multivariate optical element to determine optimal spectral elements for the sample of interest.

8. The method as in claim 1, wherein the performance is an overall system performance or a multivariate optical element performance.

9. The method as in claim 1, wherein the system components include a plurality of detectors and wherein the optimal signal-to-noise ratio is determined by evaluating expected signal levels and using a noise equivalent power of the detectors as a noise level.

10. The method as in claim 1, wherein the system components include a plurality of detectors and wherein the optimal signal-to-noise ratio is determined by evaluating an expected signal level and using photon-limited noise where photon noise associated with the signal level is sufficiently high to overwhelm detector noise.

11. The method as in claim 1, further comprising ranking the system components relative to each other to select an optimal system.

12. The method as in claim 11, further comprising manufacturing the optimal system.

13. A method of selecting spectral elements and system components for a multivariate optical analysis system, the method comprising:
   (a) providing spectral calibration data for a sample of interest;
   (b) identifying a plurality of different combinations of system components selected from the group consisting of detectors, light sources, spectral elements, and optical components;
   (c) obtaining modeling performance of a pilot system with one of the combinations of system components;
   (d) determining a prediction accuracy of the pilot system utilized in step (c);
   (e) determining measurement characteristics of the pilot system utilized in step (c);
   (f) repeating steps (c), (d) and (e) for each of the plurality of combinations identified in step (b); and
   (g) selecting optimal system components from among the plurality of combinations of system components based on optimal measurement characteristics.

14. The method as in claim 13, wherein determining optimal characteristics includes determining a prediction accuracy of the pilot system.

15. The method as in claim 13, wherein determining optimal characteristics includes determining an optimal signal-to-noise ratio of the pilot system.

16. A method of selecting spectral elements and system components for a multivariate optical analysis system, the method comprising:
   (a) providing spectral calibration data for a sample of interest;
   (b) identifying a plurality of different combinations of system components selected from the group consisting of detectors, light source, spectral elements, and optical components;
   (c) obtaining modeling performance of a pilot system with one of the combinations of system components using a multivariate optical analysis;
   (d) determining a prediction accuracy of the pilot system utilized in step (c);
   (e) determining measurement characteristics of the pilot system utilized in step (c);
   (f) repeating steps (c), (d) and (e) for each of the plurality of combinations identified in step (b);
   (g) selecting optimal system components from among the plurality of combinations of system components based on optimal measurement characteristics; and
   (h) manufacturing a multivariate optical analysis system utilizing the selected optimal system components.

17. The method as in claim 16, wherein determining optimal characteristics includes determining a prediction accuracy of the pilot system.

18. The method as in claim 16, wherein determining optimal characteristics includes determining an optimal signal-to-noise ratio of the pilot system.

19. The method as in claim 16, wherein the system components are selected from the group consisting of a plurality of detectors, a plurality of light sources, a plurality of spectral elements, a plurality of optical components and combinations thereof.

* * * * *